(12) United States Patent
Narainasamy et al.

(10) Patent No.: US 8,706,285 B2
(45) Date of Patent: Apr. 22, 2014

(54) PROCESS TO DESIGN AND FABRICATE A CUSTOM-FIT IMPLANT

(75) Inventors: Selvanathan Narainasamy, Kuala Lumpur (MY); Victor S Devadass, Kuala Lumpur (MY); Mangalam Sankupellay, Kuala Lumpur (MY); Thyaganathan Seperamaniam, Kuala Lumpur (MY); Somasundaram Nagappan, Kuala Lumpur (MY); Senthil K Selvanathan, Kuala Lumpur (MY); Nanchappan Selvanathan, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 555 days.

(21) Appl. No.: 12/747,075

(22) PCT Filed: Dec. 11, 2008

(86) PCT No.: PCT/MY2008/000188
§ 371 (c)(1),
(2), (4) Date: Sep. 19, 2010

(87) PCT Pub. No.: WO2009/075562
PCT Pub. Date: Jun. 18, 2009

(65) Prior Publication Data
US 2011/0016690 A1 Jan. 27, 2011

(30) Foreign Application Priority Data
Dec. 11, 2007 (MY) .............................. PI 20072212

(51) Int. Cl.
*A61F 2/02* (2006.01)

(52) U.S. Cl.
USPC .......... 700/118; 700/117; 700/119; 623/16.11

(58) Field of Classification Search
USPC ............... 29/896.1; 700/95, 97, 98, 118–120; 623/16.11, 17.19, 23.51, 901
See application file for complete search history.

(56) References Cited

U.S. PATENT DOCUMENTS

| | | | |
|---|---|---|---|
| 5,771,310 A * | 6/1998 | Vannah | 382/154 |
| 6,510,334 B1 | 1/2003 | Schuster et al. | |
| 6,932,842 B1 * | 8/2005 | Litschko et al. | 623/16.11 |
| 6,944,518 B2 * | 9/2005 | Roose | 700/117 |
| 6,978,188 B1 * | 12/2005 | Christensen | 700/118 |
| 7,050,877 B2 * | 5/2006 | Iseki et al. | 700/118 |
| 7,113,841 B2 * | 9/2006 | Abe et al. | 700/118 |
| 7,471,821 B2 * | 12/2008 | Rubbert et al. | 382/154 |
| 7,603,192 B2 * | 10/2009 | Martin et al. | 700/98 |
| 8,170,641 B2 * | 5/2012 | Belcher | 600/407 |
| 2004/0102866 A1 | 5/2004 | Harris et al. | |
| 2005/0089822 A1 | 4/2005 | Geng | |
| 2005/0133955 A1 * | 6/2005 | Christensen | 264/219 |
| 2006/0094951 A1 * | 5/2006 | Dean et al. | 600/407 |
| 2010/0274534 A1 * | 10/2010 | Steines et al. | 703/1 |
| 2011/0208256 A1 * | 8/2011 | Zuhars | 606/86 R |

FOREIGN PATENT DOCUMENTS

| | | |
|---|---|---|
| CA | 2373691 A1 | 3/2007 |
| DE | 3933459 A1 | 4/1991 |
| DE | 19901271 A1 | 7/2007 |

OTHER PUBLICATIONS

Sekou Singare, Li Dichen, Lu Bingheng, Liu Yanpu, Gong Zhenyu, Liu Yaxiong. "Design and fabrication of custom mandible titanium tray based on rapid prototyping." Medical Engineering & Physics (Oct. 2004), vol. 26, pp. 671-676. Abstract, pp. 672-674.

* cited by examiner

*Primary Examiner* — Minh Trinh

(74) *Attorney, Agent, or Firm* — Preston Smirman; Smirman IP Law, PLLC

(57) ABSTRACT

A process for designing and fabricating a custom-fit implant, comprising: a) processing medical image data of a patient's pathologically defective or anatomically deformed area having a symmetrical part to construct a three-dimensional (3D) digital model; b) forming a mirror image of the left or right side of the three-dimensional (3D) digital model based on its axis of symmetry depending on which side the pathologically defective or anatomically deformed area is; c) overlying the mirror image on the original image to form a composite image with a non-overlapping area wherein the implant will be fitted; d) generating a digital implant by cutting off the non-overlapping area of the mirror image; e) designing mounting points between the digital implant and the pathologically defective or anatomically deformed area where the implant is mounted thereon; f) building a positive and a negative mold based on the digital implant to fabricate a custom-fit implant.

18 Claims, No Drawings

PROCESS TO DESIGN AND FABRICATE A CUSTOM-FIT IMPLANT

CROSS-REFERENCE TO RELATED APPLICATION

The instant application claims priority to PCT International Application No. PCT/MY2008/000188, filed on Dec. 11, 2008, and Malaysian Patent Application No. P120072212, filed Dec. 11, 2007, the entire specifications of both of which are expressly incorporated herein by reference.

FIELD OF INVENTION

The present invention relates to a process for designing and fabricating a custom-fit implant. In particular, the present invention relates to a process for the design, development and fabrication of a custom-made reconstruction or implants for medical applications.

BACKGROUND OF THE INVENTION

An implant is a medical device manufactured to replace and act as a cover to a missing biological structure or to fit a pathological area of human body. Most of the implants are made up of biocompatible materials such as titanium, ceramic and others depending on what is the most functional. Medical implants are usually applied in the orthopaedic, cranioplasty, neurosurgery, oral surgery, plastic surgery and other pathological fields to repair or recontour a defect at a particular pathological area of a patient. Generally, a custom made medical implant will be an advantage considering the compatibility and precision of the implant to a patient's pathological area.

Conventionally, medical implant is shaped to a patient's pathological area at the time of surgery. Majority of medical doctors and surgeons rely only on two-dimensional (2D)-based medical images for diagnosis, treatment and surgery. These 2D based images, especially Computer Tomography (CT) and Magnetic Resonance Imaging (MRI) are generated by the medical scanners and often viewed directly from a computer terminal or printed out on film. The knowledge and experience to understanding and interpretation of these 2D images take many years of practice and intuitive thinking. In some cases, even an experienced doctor or surgeon will face great difficulty in understanding and making the right diagnosis, especially in complicated cases.

The difficulty in grasping 2D images arises when a medical practitioner has to review multiple 2D images in order to understand the precise anatomy or morphology of a three-dimensional (3D) object, such as a bone or tumor. The multiple 2D images are reconstructed in mind and conceptually converted to virtual 3D images. When carrying out a surgery, the medical practitioner will have to rely on the 2D images to map out the correct path to repair a defect without harming any other healthy parts of a patient's anatomy. This phenomenon is especially significant in the area of maxillofacial reconstruction where surgeons depend on simple measurements according to 2D images of a bony structure which are then translated into 3D object during surgery. The implants are retro-fitted onto the patient during surgery so as to fit the pathologically defective or anatomically deformed area. These approaches often result in the patient exhibiting slight deformities due to the misjudgment when forming the implants manually, which requires further surgery to repair or recontour.

Since most surgeons fixing a defect at a pathologically defective or anatomically deformed area of a patient by retro-fitting an implant at the time of surgery and with the patient's anatomy exposed, a lot of difficulties arises. These include longer surgery time, higher risk of infection and/or aesthetically unpleasing results. Therefore, some implants may have to be constructed before the surgery. In recent years, various groups around the world have been working on the design and fabrication of customized medical implants.

There are a few inventions described by the prior arts relating to a method for producing medical implants or reconstruction and the product thereof. These patented technologies include a wide variation in their manufacturing methods and qualities of the products.

Of interest in connection with a method for designing and producing a custom-fit prosthesis is U.S. Patent No. US2005133955. According to the preferred embodiment of this prior art, a mould is produced and from which a custom-fit implant may be directly or indirectly manufactured. The method described in this invention comprises the steps of receiving medical image data representing surrounding portions of a patient's anatomy to be repaired, performing 3D surface reconstruction, designing a custom-fit implant, modelling a two-part mould with a void in the shape of a custom-fit implant and outputting the two-part mould from which the custom-fit implant may be manufactured. This method focuses mainly on the manufacturing method of the mould and it is usually applied in cranioplasty.

Of interest in respect to a method for contouring bone reconstruction plates is U.S. Pat. No. 6,978,188. This invention discloses a method of producing a template for use in pre-contouring bone reconstruction plates, wherein the method comprises the steps of receiving medical image data representing surrounding portions of a patient's anatomy to be repaired, performing 3D surface reconstruction, performing virtual removal of a bony structure to be reconstructed with reference to the medical image data by stimulating the surgical implantation procedure; creating a representation of a template contoured to fit a patient's anatomy to be repaired; and outputting a replica of the template buy using Solid Free-form Fabrication manufacturing techniques. However, the recontouring process of implant is carried out at the time of surgery.

Another U.S. Patent No. US2004102866 also relates to surgical planning methods and in particular to the planning of surgical operations to implant a prosthesis. The invention uses an interactive system to design both the shape of the prosthesis and the shape of the bone. In another embodiment, a modified Marching Cubes algorithm is used to simulate cutting planes within bones. Besides, a back-projection used within a computer model to allow an integrated display of both bone and prosthesis and an interactive system used to test the mobility of a proposed implant are also embodied in this prior art. This prosthesis invented is specifically applied to knee joint.

There is also a Germany Patent No. DE3933459 relating to a biomedical implant production equipment which uses computer tomographic image to generate an implant profile for component. The complete process is based upon five different steps. The primary data are provided by a computer tomographic image and a computer is used to post process the data into a form usable by a machine tool. This invention uses a laser cutter or milling machine for the manufacture.

Another Germany Patent No. DE19901271 also relates to an implant for reconstruction of (especially cranial) bone defects comprising aluminium oxide and zirconium oxide ceramic coated with tricalcium phosphate or hydroxylapatite for good biocompatibility. The method includes inserting an implant or a mould for casting an implant into a bone defective area. The implant is prepared by using an imaging process and is coated before the insertion.

There is also a method for generating patient-specific implants disclosed by Canada Patent No. CA2373691. This invention utilizes the medical image data of a patient to generate an implant which is functionally and aesthetically adapted to the patient with a greater degree of precision. According to this invention, a virtual 3D data of a patient is compared with real medical reference data. This data bank is used as reference to create an implant.

There is no patented technology over the prior arts disclosing a method for designing and manufacturing a custom-fit medical implant based on medical scan images of a patient's pathologically defective or anatomically deformed area where the implant designed will undergo refinement to reach a high degree in its precision. Since suitably fitting implants considerably improve the health and quality of life for a patient, the development, design and fabrication of a custom made implant is essential as it provides high degree of precision to the patient's anatomy.

SUMMARY OF INVENTION

The primary object of the present invention is to provide a process for designing and fabricating a custom-fit implant with high degree of precision to the patient's anatomy.

Another object of the present invention is to develop a process to improve the accuracy in diagnosis and monitoring defect in maxillofacial, orthopaedic or forensics by using three-dimensional (3D) data.

Still another object of the present invention is to develop a process to reduce and/or rectify deformities which are attributed to the imprecision of medical implant that requires further surgery.

Yet another object of the present invention is to produce a physical or virtual model of a patient's pathologically defective or anatomically deformed area to be used for case studies or as a teaching tool.

Further object of the present invention is to provide a model of a custom-fit implant from three-dimensional data which is applicable in record keeping or as a teaching aid.

At least one of the preceding objects is met, in whole or in part, by the present invention, in which one of the embodiments of the present invention describes a process for designing and fabricating a custom-fit implant, comprising: a) processing medical image data of a patient's pathologically defective or anatomically deformed area having a symmetrical part to construct a three-dimensional (3D) digital model; b) forming a mirror image of the left or right side of the three-dimensional (3D) digital model based on its axis of symmetry depending on which side the pathologically defective or anatomically deformed area is; c) overlying the mirror image on the original image to form a composite image with a non-overlapping area wherein the implant will be fitted; d) generating a digital implant by cutting off the non-overlapping area of the mirror image; e) designing mounting points between the digital implant and the pathologically defective or anatomically deformed area where the implant is mounted thereon; and f) building a positive and a negative moulds based on the digital implant to fabricate a custom-fit implant.

Another embodiment of the present invention is a process for designing and fabricating a custom-fit implant, comprising: a) processing medical image data of a patient's pathologically defective or anatomically deformed area to construct a three-dimensional (3D) digital model; b) creating a patch representing the pathologically defective or anatomically deformed area of the digital model; wherein the patch is designed according to suitable data obtained from the digital model or from a reference digital model of another patient; c) customizing the patch into a digital implant; d) designing mounting points between the digital implant and the pathologically defective or anatomically deformed area where the implant is mounted thereon; and e) building a positive and a negative moulds based on the digital implant to fabricate a custom-fit implant.

Yet another embodiment of the present invention is a process for designing and fabricating a custom-fit implant, comprising: a) processing medical image data of a patient's pathologically defective or anatomically deformed area to construct a three-dimensional (3D) digital model; b) converting the digital model into a point cloud; c) filling up the pathologically defective or anatomically deformed area on the digital model to form a new cloud points; d) reverting the new cloud points back into a digital implant; e) designing mounting points between the digital implant and the pathologically defective or anatomically deformed area where the implant is mounted thereon; and f) building a positive and a negative moulds based on the digital implant to fabricate a custom-fit implant.

Further embodiment of the present invention is a process for designing and fabricating a custom-fit implant which further comprises a step of fabricating a physical model from the three-dimensional (3D) digital model and an intermediate physical implant to ensure that the intermediate implant closely fits the pathologically defective or anatomically deformed area on the physical model.

One skilled in the art will readily appreciate that the present invention is well adapted to carry out the objects and obtain the ends and advantages mentioned, as well as those inherent therein. The embodiments described herein are not intended as limitations on the scope of the invention.

DETAIL DESCRIPTION OF THE INVENTION

The present invention relates to a process for designing and fabricating a custom-fit implant. In particular, the present invention relates to a process for the design, development and fabrication of a custom-made reconstruction or implants for medical applications.

Hereinafter, the invention shall be described according to the preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claim.

The present invention discloses a process for designing and fabricating a custom-fit implant, comprising: a) processing medical image data of a patient's pathologically defective or anatomically deformed area having a symmetrical part to construct a three-dimensional (3D) digital model; b) forming a mirror image of the left or right side of the three-dimensional (3D) digital model based on its axis of symmetry depending on which side the pathologically defective or anatomically deformed area is; c) overlying the mirror image on the original image to form a composite image with a non-overlapping area wherein the implant will be fitted; d) generating a digital implant by cutting off the non-overlapping area of the mirror image; e) designing mounting points between the digital implant and the pathologically defective or anatomically deformed area where the implant is mounted thereon; and f) building a positive and a negative moulds based on the digital implant to fabricate a custom-fit implant.

Unlike the prior arts which mostly disclose a method for constructing an implant, the present invention focuses on the design and refinement processes to obtain a set of moulds for the fabrication of a custom-fit implant.

This invention utilizes the medical image data of a patient from clinical cases. It employs a plurality of medical imaging protocols and computer software to design a 3D digital model which offers better treatment outcome for traumatic injuries. Preferably, this process is applied in the maxillofacial reconstruction for a particular pathologically defective or anatomically deformed area or a defective area, which caused by pathological or other factors.

According to the preferred embodiment of the present invention, a patient's medical image data is obtained from a medical imaging scanner. The area scanned includes the defective/deformed anatomical area as well as the surrounding areas. In accordance with the preferred embodiment, the medical image data is preferably a computer tomography (CT) scan or a magnetic resonance imaging (MRI) scan. In the most preferred embodiment of the present invention, the medical image data is a CT scan. This two-dimensional (2D) medical image data is processed by conventional imaging processing software before it is used for the design of an implant.

The process embodied herein is initiated by processing this medical image data to produce segmented slices of the bony structure for a particular pathologically defective or anatomically deformed area as described by the preferred embodiment. Preferably, the 2D medical image data is processed and segmented by using thresholding algorithm and followed by region growing method. The bone segment is extracted from every slice of the medical scan data. Consequently, a three-dimensional (3D) digital model for a particular pathologically defective or anatomically deformed area is constructed based on the segmented 2D slices. According to the preferred embodiment of the present invention, a 3D digital construction technique is applied for the construction of the 3D digital model.

It is desired in the preferred embodiment that the present invention includes a step of forming a mirror image of the 3D digital model for the designing of a digital implant. The mirror image of the left or right side of the 3D surface model is formed based on the axis of symmetry of the 3D digital model, depending on which side the pathologically defective or anatomically deformed area is. The mirror image is then overlaid on the original image to form a composite image with a non-overlapping area wherein the implant will be fitted. For example, when a pathologically defective or anatomically deformed area is located at the right side, a mirror image of the right side will be constructed. Then, this mirror image will be overlaid on the original image of the left side to form the composite image. A non-overlapping area which is the pathologically defective or anatomically deformed area is identified on the composite image. A digital implant is generated by cutting off the non-overlapping area of the mirror image with the application of CAD tools by following the contour of the non-overlapping area.

The mirror image is formed based on the axis of symmetry of the surface model. Nevertheless, most human cranial structures are not perfectly symmetrical and the asymmetry parts will result in an imperfect match. As such, the digital implant will have to be refined manually so that match the asymmetrical structure. Another embodiment of the present invention is a step of designing mounting points between the implant and the pathologically defective or anatomically deformed area where the implant is mounted thereon. For those locations where the mounting points are not sufficiently strong to support the implant, modification and refinement is preferably to be performed. A slight extension of the implants can increase the integrity between the implant and the pathologically defective or anatomically deformed area. Further refinements on the 3D digital model using a graphic pen is preferably performed for a close fit.

One person skilled in the art shall appreciate the fact that, once the modified digital implant design has been completed, it is then checked if it fits and mounts with the original pathologically defective or anatomically deformed area correctly and firmly, a process called 'registration'. This step is preferably carried out by 'fitting' the digital implant with the 3D digital model of the pathologically defective or anatomically deformed area created earlier. If the implant does not fit correctly, i.e. it does not 'register' with the original model, it then undergoes further refinement.

In accordance with the preferred embodiment of the present invention, a positive and a negative digital moulds are built based on the refined intermediate implant. The positive and negative physical moulds are built by casting over the implant pattern as described by one of the preferred embodiment. The moulds are then used for the fabrication of a custom-fit implant.

Consequently, the fabricating step is performed by stamping the moulds with a biocompatible material to obtain the custom-fit implant as described by the preferred embodiment. According to the preferred embodiment of the present invention, the biocompatible material is preferably to be titanium. The implant with the accurate shape of a custom-fit implant is obtained by pressing the positive and negative mould with the titanium mesh in between the moulds. During the stamping process, small and measured cuts are made in certain locations on the plate so as to ensure that "kinks" are not formed. By making these cuts, a smooth formation of the implant takes place. Finally, the stamped plate is cut appropriately to remove excess material. These processes allow the stamped plate to be substantially identical to the peripheral shape of the defect or the anatomically deformed area so as to ensure a very close fit and mounts properly. It reduces the necessity for manipulation and adjustment during surgery.

In another embodiment of the present invention, the process for designing and fabricating a custom-fit implant further comprises a step of fabricating a physical model of the whole pathologically defective or anatomically deformed area and an intermediate physical implant from the three-dimensional (3D) digital model to ensure that the intermediate implant closely fits the pathologically defective or anatomically deformed area on the physical model. This process is performed before the titanium implant is made. The intermediate physical implant is an unrefined implant which will be further refined manually by hand. Preferably, this 3D physical model of the particular pathologically defective or anatomically deformed area is fabricated using Rapid Prototyping Technology using the stereolithographic (STL) format and an intermediate implant is designed and fabricated in such a manner as well. This intermediate implant can be fitted to the physical model created earlier to confirm whether it fits accurately and precisely.

Further embodiment of the present invention is a process for designing and fabricating a custom-fit implant which further comprises a step of modifying the intermediate physical implant to make a mould for the custom-fit implant. If the intermediate implant does not precisely fit the pathologically defective or anatomically deformed area of the physical model, further modification will be performed. The process of modification is manually performed and it varies according to the anatomical differences among the cases.

Many contours meeting at a single point will result in sharp edges on the implant, especially when metal implants are involved. Therefore, a modification step which involves the application of the multiple contouring technique on the intermediate physical implant is carried out to reduce the occurrence of these sharp edges as described by the preferred embodiment of the present invention. Multiple contouring technique is performed by dipping tissues (paper meche) into a photo polymer resin and followed by laying multiple layers of these tissues over the sharp edges of the intermediate physical implant to smoothen the transition of the edges. The remaining sharp corners or kinks are buffed and ground down.

According to one of the preferred embodiments, the modified implant is optically scanned so as to create a new set of digital CAD data in the computer. A new modified intermediate implant is then fabricated and placed over the defective region of the model to confirm the fitting. It is envisioned that one skilled in the art may repeat this process as often as necessary until proper design and fitting is achieved. Once the proper fitting is achieved, the intermediate implant is then used as a pattern or a master to create the moulds, both the core and cavity, which will be used to fabricate the final implant.

A person skilled in the art should appreciate the fact that virtual models will be used to design and manufacture the implants in the cases where the defect of an anatomical area is minor and can be easily modeled and modified in the computer. On the other hand, an intermediate physical model of the defective region is constructed in the complicated cases using Rapid Prototyping Technology. Preferably, the implant is manipulated and sculptured manually to fit the model before it is used on the actual patient. In one of the preferred embodiment of the present invention, tissue paper is preferably dipped into resin and then layered over the intermediate implant. It is then sculptured by hand to form the preferred profile of the implant. The modified implant, is then dried using ultraviolet light until it has hardened. An optical scan of the altered intermediate physical implant is carried and a new set of a digital CAD data is captured. The close fit, of the titanium mesh into the pathologically defective or anatomically deformed area helps to improve the growth of the bone tissue which is then bonded to the implant. Moreover, the structural integrity of the bony structure with the treated pathologically defective or anatomically deformed area is also enhanced.

Another embodiment of the present invention is a process for designing and fabricating a custom-fit implant, comprising: a) processing medical image data of a patient's pathologically defective or anatomically deformed area to construct a three-dimensional (3D) digital model; b) creating a patch representing the pathologically defective or anatomically deformed area of the digital model; wherein the patch is designed according to suitable data obtained from the digital model or from a reference digital model of another patient; c) customizing the patch into a digital implant; d) designing mounting points between the digital implant and the pathologically defective or anatomically deformed area where the implant is mounted thereon; and e) building a positive and a negative moulds based on the digital implant to fabricate a custom-fit implant.

In accordance to this preferred embodiment, the process for designing and fabricating a custom-fit implant comprising processing medical image data of a patient's pathologically defective or anatomically deformed area to construct a 3D digital model as set forth in the preceding description. Consequently, a patch representing the pathologically defective or anatomically deformed area of the digital model is created. This patch is designed according to suitable data obtained from the digital model of the same patient or from a reference digital model of another patient. According to the preferred embodiment of the present invention, the reference digital model of another patient used is preferably having similar morphological data that is applicable for the creation of the patch. The patch is then customized into a digital implant according to the pathologically defective or anatomically deformed area on the 3D digital model for the particular patient.

This preferred embodiment is more applicable to fabricate implant for those pathologically defective or anatomically deformed areas which do not possess a symmetrical part, for instance at the middle part of the cranium or the mandible. After customization of the patch into the digital implant, the mounting points between the digital implant and the physical model is designed precisely so as to ensure a close fit when the digital implant is fabricated and mounted on the pathologically defective or anatomically deformed area later. The fabrication of the digital implant is based on the shapes of the positive and the negative moulds built, as described by the preceding description. As set forth in the foregoing description, an intermediate physical implant and a physical model of the pathologically defective or anatomically deformed area can also be fabricated to ensure the proper fitting and mounting of the custom-fit implant on the physical model.

Further embodiment of the present invention is a process for designing and fabricating a custom-fit implant, comprising: a) processing medical image data of a patient's pathologically defective or anatomically deformed area to construct a three-dimensional (3D) digital model; b) converting the digital model into a point cloud; c) filling up the pathologically defective or anatomically deformed area on the digital model to form a new cloud points; d) reverting the new cloud points back into a digital implant; e) designing mounting points between the digital implant and the pathologically defective or anatomically deformed area where the implant is mounted thereon; and f) building a positive and a negative moulds based on the digital implant to fabricate a custom-fit implant.

The point cloud method embodied herein is preferably to be used for the mild pathologically defective or anatomically deformed or defective cases which an anatomically simple implant with a smaller surface area is required for the reconstruction.

The custom-fit implant designed and fabricated by the present invention is applicable to various fields. It is especially useful in the maxillofacial reconstruction as the physical model will help the medical practitioners to plan their approach to reconstruct a pathologically defective or anatomically deformed area of their patient's body. The implant can be custom made to fit a specific patient before surgery by using both the physical and virtual models.

Besides, the 3D surface model can also be applied in designing patient-specific implants for orthopaedic reconstruction, such as ball replacement and femur nails. It is also applicable in forensic research. Besides, both the physical and the virtual 3D surface models of the present invention can be used as a teaching aid. Apart form that, the 3D models can be archived as a permanent record of rare and interesting anatomical disorders.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

The invention claimed is:

1. A process for designing and fabricating a custom-fit implant, comprising the steps of:
   a) processing medical image data of a patient's pathologically defective or anatomically deformed area having a symmetrical part to construct a computer-generated original image of a three-dimensional (3D) digital model;
   b) forming a mirror image of a left or a right side of the three-dimensional (3D) digital model based on its axis of symmetry depending on which side the pathologically defective or anatomically deformed area is;
   c) overlying the mirror image on the original image of the three-dimensional (3D) digital model to form a composite image with a non-overlapping area wherein the custom-fit implant will be fitted;
   d) forming a computer-generated digital image of an implant by cutting off the non-overlapping area of the mirror image;
   e) designing mounting points between the digital image of the implant and the pathologically defective or anatomically deformed area where the custom-fit implant is to be mounted thereon; and
   f) building a positive and a negative mould based on the digital image of the implant to fabricate the custom-fit implant.

2. The process as claimed in claim 1, further comprising the step of fabricating a physical model and an intermediate physical implant from the three-dimensional (3D) digital model to ensure that the intermediate implant closely fits the anatomically deformed area on the physical model.

3. The process as claimed in claim 2, wherein the physical model is fabricated by a rapid prototyping process with stereolithography (STL) format.

4. The process as claimed in claim 1, wherein the medical image data is a computer tomography (CT) or a magnetic resonance imaging (MRI) scan.

5. The process as claimed in claim 1, wherein the three-dimensional (3D) digital model is constructed by computer-aided design (CAD) software.

6. The process as claimed in claim 1, wherein the custom-fit implant is fabricated by stamping the moulds with a titanium mesh.

7. A process for designing and fabricating a custom-fit implant, comprising the steps of:
   a) processing medical image data of a patient's pathologically defective or anatomically deformed area to construct a computer-generated three-dimensional (3D) digital model;
   b) creating a patch representing the pathologically defective or anatomically deformed area of the digital model, wherein the patch is designed according to data obtained from the three-dimensional (3D) digital model or from a reference digital model of another patient;
   c) shaping the patch so as to form a computer-generated digital image of an implant;
   d) designing mounting points between the digital image of the implant and the pathologically defective or anatomically deformed area where the custom-fit implant is to be mounted thereon; and
   e) building a positive and a negative mould based on the digital image of the implant to fabricate the custom-fit implant.

8. The process as claimed in claim 7, further comprising the step of fabricating a physical model and an intermediate physical implant from the three-dimensional (3D) digital model to ensure that the intermediate implant closely fits the anatomically deformed area on the physical model.

9. The process as claimed in claim 8, wherein the physical model is fabricated by a rapid prototyping process with stereolithography (STL) format.

10. The process as claimed in claim 7, wherein the medical image data is a computer tomography (CT) or a magnetic resonance imaging (MRI) scan.

11. The process as claimed in claim 7, wherein the three-dimensional (3D) digital model is constructed by computer-aided design (CAD) software.

12. The process as claimed in claim 7, wherein the custom-fit implant is fabricated by stamping the moulds with a titanium mesh.

13. A process for designing and fabricating a custom-fit implant, comprising the steps of:
   a) processing medical image data of a patient's pathologically defective or anatomically deformed area to construct a computer-generated three-dimensional (3D) digital model;
   b) converting the digital model into a first point cloud, wherein the first point cloud comprises a first set of data points in a three-dimensional coordinate system;
   c) filling up the pathologically defective or anatomically deformed area on the digital model to form a second point cloud, wherein the second point cloud comprises a second set of data points in a three-dimensional coordinate system;
   d) reverting the second cloud point back into a computer-generated digital image of an implant;
   e) designing mounting points between the digital image of the implant and the pathologically defective or anatomically deformed area where the custom-fit implant is to be mounted thereon; and
   f) building a positive and a negative mould based on the digital image of the implant to fabricate the custom-fit implant.

14. The process as claimed in claim 13, further comprising the step of fabricating a physical model and an intermediate physical implant from the three-dimensional (3D) digital model to ensure that the intermediate implant closely fits the anatomically deformed area on the physical model.

15. The process as claimed in claim 14, wherein the physical model is fabricated by a rapid prototyping process with stereolithography (STL) format.

16. The process as claimed in claim 13, wherein the medical image data is a computer tomography (CT) or a magnetic resonance imaging (MRI) scan.

17. The process as claimed in claim 13, wherein the three-dimensional (3D) digital model is constructed by computer-aided design (CAD) software.

18. The process as claimed in claim 13, wherein the custom-fit implant is fabricated by stamping the moulds with a titanium mesh.

* * * * *